(12) United States Patent
Lukas et al.

(10) Patent No.: US 9,446,057 B2
(45) Date of Patent: *Sep. 20, 2016

(54) CONTROLLED RELEASE DOXYCYCLINE

(71) Applicant: Mayne Pharma International Pty Ltd., Salisbury South (SA)

(72) Inventors: Stefan Lukas, Manningham (AU); Angelo Lepore, Rostrevor (AU); Stuart Mudge, Northcote (AU)

(73) Assignee: Mayne Pharma International Pty. Ltd., Salisbury South (AU)

( * ) Notice: Subject to any disclaimer, the term of this patent is extended or adjusted under 35 U.S.C. 154(b) by 61 days.

This patent is subject to a terminal disclaimer.

(21) Appl. No.: 14/939,936

(22) Filed: Nov. 12, 2015

(65) Prior Publication Data

US 2016/0101119 A1 Apr. 14, 2016

Related U.S. Application Data (63) Continuation of application No. 14/521,998, filed on Oct. 23, 2014.

(60) Provisional application No. 62/061,481, filed on Oct. 8, 2014.

(51) Int. Cl.
*A61K 9/50* (2006.01)
*A61K 31/65* (2006.01)

(52) U.S. Cl.
CPC ............. *A61K 31/65* (2013.01); *A61K 9/5047* (2013.01)

(58) Field of Classification Search
CPC .... A61K 9/16; A61K 9/1605; A61K 9/1611; A61K 9/1617; A61K 9/1629
USPC ................................................. 424/489–502
See application file for complete search history.

(56) References Cited

U.S. PATENT DOCUMENTS

| | | |
|---|---|---|
| 6,958,161 B2 | 10/2005 | Hayes et al. |
| 7,232,572 B2 | 6/2007 | Ashley |
| 7,910,128 B2 | 3/2011 | Chang et al. |
| 8,603,506 B2 | 12/2013 | Ashley |
| 8,652,516 B1 | 2/2014 | Etchegaray et al. |
| 2004/0142035 A1 | 7/2004 | Chang et al. |
| 2004/0228912 A1 | 11/2004 | Chang et al. |
| 2012/0100214 A1 | 4/2012 | Segura et al. |

*Primary Examiner* — Micah-Paul Young
(74) *Attorney, Agent, or Firm* — Cooley LLP (57) ABSTRACT

The disclosure provides controlled release compositions comprising tetracyclines and in some embodiments, doxycycline. The controlled release doxycycline compositions of the invention exhibit a superior dissolution profile and provide reduce side effects such as nausea and irritation.

27 Claims, 6 Drawing Sheets

CONTROLLED RELEASE DOXYCYCLINE

CROSS REFERENCE TO RELATED APPLICATIONS

The present Application is a continuation of U.S. application Ser. No. 14/521,998, filed Oct. 23, 2014, which claims priority to U.S. Provisional Application No. 62/061,481, filed on Oct. 8, 2014, the entire contents of each of which are hereby incorporated by reference in their entirety.

FIELD

The present disclosure relates to the field of pharmaceutical compositions comprising tetracyclines. In specific aspects, the disclosure provides pharmaceutical compositions comprising doxycycline that have improved controlled release characteristics.

BACKGROUND

Tetracyclines, such as doxycycline, are used as broad spectrum antibiotics to treat various bacterial infections. Tetracyclines interfere with the protein synthesis of Gram positive and Gram-negative bacteria by preventing the binding of aminoacyl-tRNA to the ribosome. Their action is bacteriostatic (preventing growth of bacteria) rather than killing (bactericidal). The doses commonly used for doxycycline to achieve the antibiotic effect are 100 mg and 50 mg.

Doxycycline, as well as other tetracyclines, has other therapeutic uses in addition to its antibiotic properties. For example, doxycycline is known to inhibit the activity of collagen destruction enzymes such as collagenase, gelatinase, and elastase. Its collagenase inhibition activity has been used to treat periodontal disease.

Doxycycline can also inhibit lipase produced by the bacterium Propionibacterium acnes and thus reduces the availability of free fatty acids that are involved in inflammation. Doxycycline may also reduce inflammation by reducing cytokine levels so that the integrity of the follicular wall is preserved. Thus, doxycycline has the potential in treating skin diseases, such as acne.

While tetracyclines have proven to be very beneficial and successful antibiotics, this class of compounds suffers from a major drawback associated with administration. Namely, tetracycline antibiotics cause an undesirable degree of gastrointestinal irritation and nausea in subjects taking the medications.

The nausea associated with administration of many tetracyclic antibiotics results from the release of the tetracycline into the lumen of an individual's stomach after ingestion. Since many tetracycline antibiotics are formulated as immediate release tablets, such antibiotic formulations begin to release antibiotic immediately upon administration and release high concentrations of tetracycline upon entering the acidic environment of a patient's stomach. The high localized concentration of the antibiotic in the patient's stomach leads to irritation and nausea.

There have been attempts to provide delayed or extended release pharmaceutical formulations of tetracyclic antibiotics that do not release in an individual's stomach, but rather release in the colon. However, many of these formulations suffer from inadequate dissolution profiles that do not provide an effective dose of antibiotic at the desired concentration and for the desired period of release.

Thus, there is a great need in the art for the development of improved controlled release pharmaceutical formulations of tetracyclic antibiotics.

More particularly, there is a need in the art for controlled release doxycycline antibiotic formulations that provide clinically effective doses of doxycycline with reduced stomach irritation and nausea.

BRIEF SUMMARY

The present disclosure addresses a crucial need in the art, by providing a controlled release pharmaceutical formulation comprising doxycycline. The controlled release doxycycline formulations of the present invention exhibit less than about 10% release of doxycycline at pH levels found in the stomach (e.g., at a pH of about 1.2) when measured after 1 hour under USP <711> conditions, and maintain low release levels at pH values up to 4.5, but have release rates at pH 5 that enable a clinically effective plasma level to be achieved.

The dissolution or release profile of the doxycycline formulations of the present invention is superior to the release profiles of other doxycycline formulations presently in the art. The advantages associated with the disclosure's release profile include, inter alia: increased efficacy of the antibiotic, increased tolerability, and ultimately increased patient compliance with drug administration.

DETAILED DESCRIPTION

Provided herein are pharmaceutical compositions comprising a tetracycline antibiotic. In most embodiments, the pharmaceutical composition comprises doxycycline.

Also provided herein are methods of treating a patient in need thereof with the pharmaceutical compositions of the present invention. In various aspects, the patients are treated for bacterial infections. In particular aspects, the patients are treated with pharmaceutical compositions according to the present invention to control skin conditions. A non-limiting list of skin conditions treatable with the pharmaceutical compositions of the present invention includes skin infections, rosacea, acne, papules, pustules, open comedo, closed comedo, etc., including combinations thereof.

While the following terms are believed to be well understood by one of ordinary skill in the art, the following definitions are set forth to facilitate explanation of the presently disclosed subject matter.

The verb "comprise" and its conjugations, are used in the open and non-limiting sense to mean that items following the word are included, but items not specifically mentioned are not excluded "About" in reference to a numerical value refers to the range of values somewhat less or greater than the stated value, as understood by one of skill in the art. For example, the term "about" could mean a value ranging from plus or minus a percentage (e.g., ±1%, 2%, or 5%) of the stated value. Furthermore, since all numbers, values, and expressions referring to quantities used herein are subject to the various uncertainties of measurement encountered in the art, then unless otherwise indicated, all presented values may be understood as modified by the term "about."

As used herein, the articles "a," "an," and "the" may include plural referents unless otherwise expressly limited to one-referent, or if it would be obvious to a skilled artisan from the context of the sentence that the article referred to a singular referent.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include any and all subranges between the minimum value of 1 and the maximum value of 10. Exemplary subranges of the range "1 to 10" include, but are not limited to, e.g., 1 to 6.1, 3.5 to 7.8, and 5.5 to 10.

As used herein, the term "polymer" is meant to encompass both natural and synthetic macromolecules, including e.g., homopolymers (polymers having only one type of repeating unit), copolymers (a polymer having more than one type of repeating unit), graft copolymers, block copolymers, etc.

"Biodegradable polymer" means a polymer or polymers, which degrade in vivo, under normal physiological conditions. The erosion of a biodegradable polymer over time occurs concurrent with, or subsequent to, release of the therapeutic agent.

The terms "biodegradable" and "bioerodible" are used interchangeably herein. A biodegradable polymer may be a homopolymer or a copolymer.

As used herein, the term "matrix" denotes a solid mixture composed of a continuous phase (often of a dissolvable or biodegradable polymer), and one or more dispersed phase(s) (e.g., particles of the pharmaceutically active ingredient such as a tetracycline, specifically doxycycline). A "polymer matrix" may refer to a matrix in which the continuous phase is a single polymer or a mixture of polymers. The mixture of polymers may be of the same class, e.g. two different PLA polymers, or of different classes, e.g. PLA polymers combined with PLGA polymers.

By "immediate release" formulation is meant a dosage form that is intended to release substantially the entire dose of active ingredient on administration with no enhanced, delayed, controlled, sustained, or extended release effect, generally over a short period of time (e.g., 30 minutes).

As discussed herein, conventional "immediate release" tetracycline-containing pharmaceutical compositions which release the tetracycline in the stomach cause nausea and irritation which can reduce compliance by patients in need of such drugs. "Controlled-release" refers to a release profile which differs from "immediate release" in that the drug is released more slowly and/or after a delay or lag time such that the release of the tetracycline in the stomach is avoided.

In most embodiments, the sustained release composition of doxycycline is in solid form, for example a granulate (e.g., aggregated particles containing doxycycline, produced by wet or dry granulation processes), drug layered beads (e.g., doxycycline coated onto an inert core particle, such as a sugar bead or nonpareil, optionally including a binder to promote adhesion of the doxycycline to the core particle), or matrix composition (e.g., doxycycline incorporated into a biodegradable/bioerodible, or soluble polymeric continuous phase).

As used herein, the term "patient" refers to an animal who is to be administered a pharmaceutical composition as taught herein. The animal may be a mammal, such as a human.

"Therapeutically effective amount" means a level or amount of an agent needed to treat a condition. Thus, a therapeutically effective amount of a therapeutic agent, such as doxycycline, is an amount that is effective in reducing at least one symptom of a patient.

For example, a "therapeutically effective amount" of doxycycline is meant that amount of doxycycline, or its pharmaceutically acceptable salt, which either maintains or reduces the severity of a condition or symptom treatable with doxycycline. The therapeutically effective amount is determined by an ordinarily skilled artisan, taking into account various considerations, such as: the age of the subject, the weight of the subject, the condition of the subject, the type of subject (i.e., the type of animal), the regimen, the desired result, and the like.

The terms "therapeutic agent", "active agent", "drug", and "active pharmaceutical ingredient" are used interchangeably herein.

Tetracyclines are a group of broad-spectrum antibiotics named for their four ("tetra-") hydrocarbon rings ("-cycl-") derivation ("-ine"). To be specific, they are defined as a subclass of polyketides having an octahydrotetracene-2-carboxamide skeleton. They are collectively known as derivatives of polycyclic naphthacene carboxamide.

The structure of Tetracycline can be found below:

(4S,6S,12aS)-4-(dimethylamino)-3,6,10,12,12a-
pentahydroxy-6-methyl-1,11-dioxo-1,4,4a,5,5a,
6,11,12a-octahydrotetracene-2-carboxamide Doxycycline is an antibiotic useful for the treatment of a number of infections. It is in the tetracycline antibiotic class. Doxycycline formulations are sold commercially under a variety of names, including: DORYX®, VIBRAMYCIN®, MONODOX®, MICRODOX® PERIOSTAT® VIBRA-TABS®, ORACEA®, VIBROX®, ADOXA®, DOXY-HEXAL®, DOXYLIN®, DOXORAL®, DOXY-1®, AND ATRIDOX®. The term "doxycycline" as used herein includes salts of doxycycline (below) including pharmaceutically acceptable salt, solvates, or solvated salts of doxycycline.

The structure of doxycycline can be found below:

(4S,4aR,5S,5aR,6R,12aS)-4-(dimethylamino)-
3,5,10,12,12a-pentahydroxy-6-methyl-
1,11-dioxo-1,4,4a,5,5a,6,11,12a-
octahydrotetracene-2-carboxamide hydrate The most common forms of doxycycline used in commercial pharmaceutical formulations include the monohydrate form and the hyclate form. The monohydrate is the base molecule hydrated with one molecule of water and is used in the formulation of capsules and, in some markets, powder oral suspensions (to be reconstituted with water). The hyclate is a hydrochloric acid salt solvated with water and ethanol and is typically used in the formulation of capsules or tablets.

The structure of doxycycline hyclate is found below:

with a molecular formula of $C_{22}H_{24}N_2O_8$, HCl, $\frac{1}{2}C_2H_6O$, $\frac{1}{2}H_2O$ and a molecular weight of 512.9.

The chemical designation for doxycycline hyclate is [4S (4aR,5S,5aR,6R,12aS)]-4-(dimethylamino)-1,4,4a,5,5a,6, 11,12a-octahydro-3,5,10,12,12a-pentahydroxy-6-methyl-1, 11-deoxonapthtacene-2-carboxamide monohydrochloride, compound with ethyl alcohol (2:1), monohydrate. Doxycycline hyclate is a yellow crystalline powder soluble in water and in solutions of alkali hydroxides and carbonates. Doxycycline has a high degree of lipid solubility and a low affinity for calcium binding. It is highly stable in normal human serum. Doxycycline will not degrade into an epianhydro form.

U.S. Pat. Nos. 6,958,161 and 8,715,724, disclose various embodiments of doxycycline compositions and methods of making and using the same. The disclosures of each of these patents are herein incorporated by reference in their entireties for all purposes.

Further, U.S. Pat. Nos. 8,470,364; 8,394,406; 8,394,405; 8,206,740; 7,910,128; 7,749,532; 8,603,506; 7,232,572; 8,652,516; and U.S. Patent Application Publication US20120100214 (U.S. application Ser. No. 13/278,989); and PCT Publication No. WO2012059338, disclose various embodiments of doxycycline compositions and methods of making and using the same. The disclosures of each of these documents are herein incorporated by reference in their entireties for all purposes.

Doxycycline is virtually completely absorbed after oral administration. For instance, following single and multiple-dose administration of DORYX Tablets, 200 mg to adult volunteers, average peak plasma doxycycline concentration ($C_{max}$) was 4.6 mcg/mL and 6.3 mcg/mL, respectively with median $T_{max}$ of 3 hours; the corresponding mean plasma concentration values 24 hours after single and multiple doses were 1.5 mcg/mL and 2.3 mcg/mL, respectively.

Further, following a 200 mg dose, normal adult volunteers averaged peak serum levels of 2.6 mcg/mL of doxycycline at 2 hours decreasing to 1.45 mcg/mL at 24 hours. Excretion of doxycycline by the kidney is about 40%/72 hours in individuals with normal function (creatinine clearance about 75 mL/min). This percentage excretion may fall as low as 1-5%/72 hours in individuals with severe renal insufficiency (creatinine clearance below 10 mL/min).

The mean $C_{max}$ and $AUC_{0-\infty}$ of doxycycline are 24% and 13% lower, respectively, following single dose administration of DORYX Tablets, 100 mg with a high fat meal (including milk) compared to fasted conditions.

The mean $C_{max}$ of doxycycline is 19% lower and the $AUC_{0-\infty}$ is unchanged following single dose administration of DORYX Tablets, 150 mg with a high fat meal (including milk) compared to fasted conditions.

Doxycycline bioavailability from DORYX Tablets, 200 mg was not affected by food, but the incidence of nausea was higher in fasted subjects. The 200 mg tablets may be administered without regard to meals.

The compositions of the present invention provide $AUC_{0-\infty}$ values within 80-125% of the following:

The compositions of the present invention provide $AUC_{0-\infty}$ values within 80-125% of 10000-24000 ng·hr/ml following administration of a 60 mg dose under fasting conditions.

The compositions of the present invention provide $AUC_{0-\infty}$ values within 80-125% of 15000-36500 ng·hr/ml following administration of a 90 mg dose under fasting conditions.

The compositions of the present invention provide $AUC_{0-\infty}$ values within 80-125% of 20000-48500 ng·hr/ml following administration of a 120 mg dose under fasting conditions.

The compositions of the present invention provide $C_{max}$ values within 80-125% of 625-1600 ng/ml following administration of a 60 mg dose under fasting conditions.

More particularly, the compositions of the present invention provide $C_{max}$ values within 80-125% of 725-1600 ng/ml following administration of a 60 mg dose under fasting conditions The compositions of the present invention provide $C_{max}$ values within 80-125% of 940-2400 ng/ml following administration of a 90 mg dose under fasting conditions.

More particularly, the compositions of the present invention provide $C_{max}$ values within 80-125% of 1100-2400 ng/ml for a 90 mg dose.

The compositions of the present invention provide $C_{max}$ values within 80-125% of 1250-3200 ng/ml following administration of a 120 mg dose under fasting conditions.

More particularly, the compositions of the present invention provide $C_{max}$ values within 80-125% of 1450-3200 ng/ml following administration of a 120 mg dose under fasting conditions.

In addition, the compositions of the present invention have pharmacokinetic characteristics which differ from that of conventional formulations which have essentially the same (e.g., bioequivalent) $AUC_{0-\infty}$ values, particularly shortly after administration. For example, 90 mg doxycycline compositions according to the present invention are bioequivalent to conventional 75 mg DORYX compositions. However, compositions according to the present invention can have $AUC_{0-0.5\ hr}$ values of about 0 ng·hr/ml, compared to about 20 ng·hr/ml for DORYX; $AUC_{0-0.75\ hr}$ values of about 5-60 ng·hr/ml, compared to about 100 ng·hr/ml for DORYX; $AUC_{0-1\ hr}$ values of about 40-200 ng·hr/ml, compared to about 270 ng·hr/ml for DORYX; $AUC_{0-1.5\ hr}$ values of about 200-650 ng·hr/ml, compared to about 800 ng·hr/ml for DORYX; $AUC_{0-2\ hr}$ values of about 600-1250 ng·hr/ml, compared to about 1500 ng·hr/ml for DORYX; $AUC_{0-2.5\ hr}$ values of about 1100-2000 ng·hr/ml, compared to about 2200 ng·hr/ml for DORYX; $AUC_{0-3\ hr}$ values of about 1800-2700 ng·hr/ml, compared to about 3000 ng·hr/ml for DORYX; $AUC_{0-3.5\ hr}$ values of about 2500-3500 ng·hr/ml, compared to about 3700 ng·hr/ml for DORYX; $AUC_{0-4\ hr}$ values of about 3100-4200 ng·hr/ml, compared to about 4400 ng·hr/ml for DORYX; $AUC_{0-4.5\ hr}$ values of about 3800-5000 ng·hr/ml, compared to about 5200 ng·hr/ml for DORYX; $AUC_{0-5\ hr}$ values of about 4500-5700 ng·hr/ml, compared to about 5900 ng·hr/ml for DORYX; $AUC_{0-5.5\ hr}$ values of about 5100-6500 ng·hr/ml, compared to about 6500 ng·hr/ml for DORYX; $AUC_{0-6\ hr}$ values of about 5700-7000 ng·hr/ml, compared to about 7100 ng·hr/ml for DORYX; $AUC_{0-8\ hr}$ values of about 7500-9000 ng·hr/ml, compared to about 9000 ng·hr/ml for DORYX; $AUC_{0-12\ hr}$ values of about 10000-12000 ng·hr/ml, compared to about 12000 ng·hr/ml for DORYX; $AUC_{0-16\ hr}$ values of about 12000-15000 ng·hr/ml, compared to about 14000 ng·hr/ml for DORYX; $AUC_{0-24\ hr}$ values of about 16000-19000 ng·hr/ml, compared to about 18000 ng·hr/ml for DORYX; $AUC_{0-36\ hr}$ values of about 20000-23000 ng·hr/ml, compared to about 22000 ng·hr/ml for DORYX; $AUC_{0-48\ hr}$ values of about 22000-26000 ng·hr/ml, compared to about 25000 ng·hr/ml for DORYX; $AUC_{0-72\ hr}$ values of about 24000-29000 ng·hr/ml, compared to about 27000 ng·hr/ml for DORYX; and $AUC_{0-96\ hr}$ values of about 25000-29000 ng·hr/ml, compared to about 28000 ng·hr/ml for DORYX.

Figure 1:
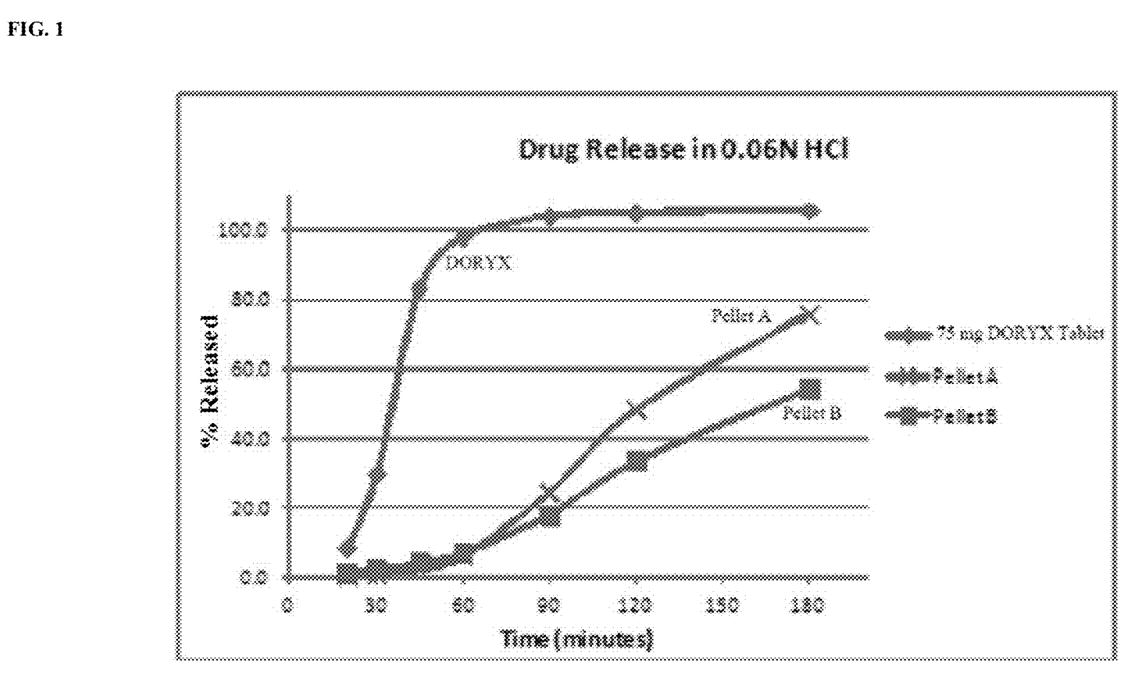
FIG. 1 is a graph illustrating the dissolution profile in acidic conditions of a controlled release pellet formulation (A or B) of the disclosure compared to a control DORYX tablet.
Figure 2:
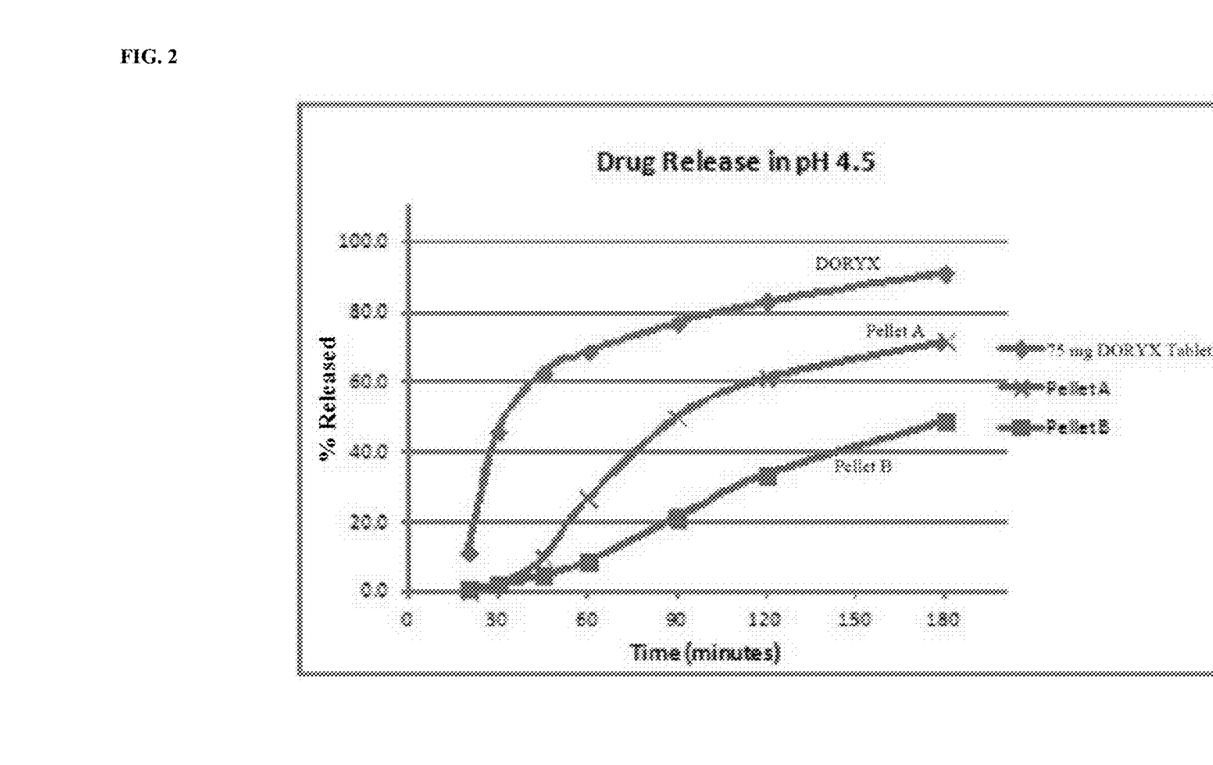
FIG. 2 is a graph illustrating the dissolution profile in basic conditions of a controlled release pellet formulation (A or B) of the disclosure compared to a control DORYX tablet.
Figure 5:
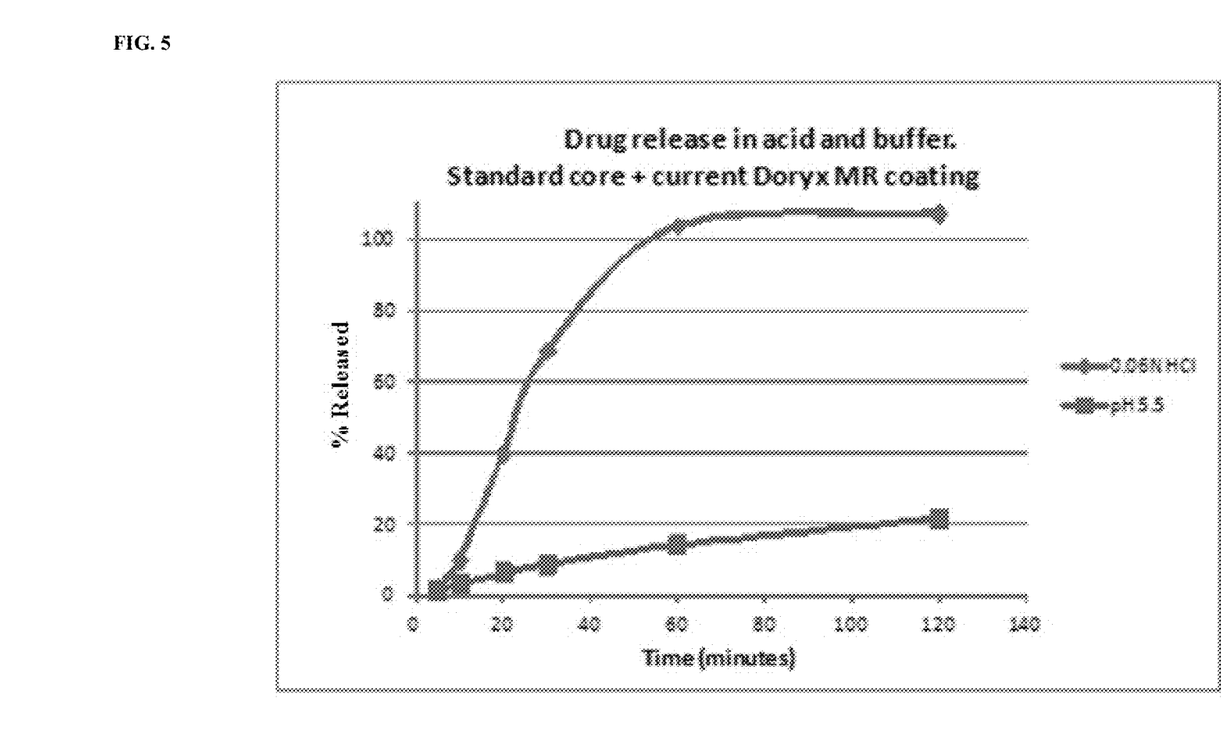
FIG. 5 is graph of an embodiment of the invention comprising doxycycline monohydrate salt, demonstrating that said embodiment is very soluble at lower pH values and releases readily under acidic conditions, but is not very soluble at pH values above 3, leading to low release rates overall.
Figure 6:
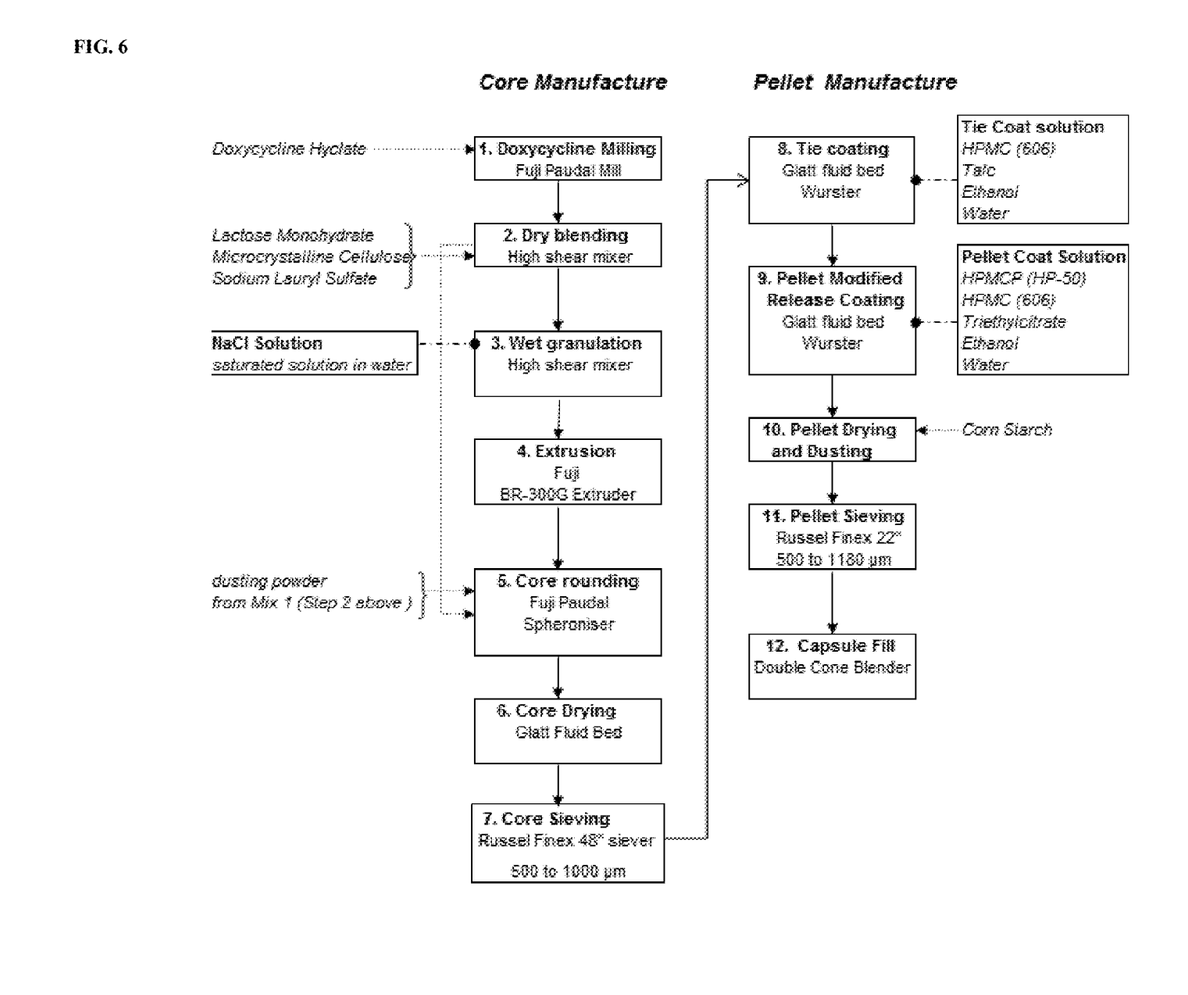
FIG. 6 is a process flow chart of a manufacturing procedure for producing embodiments of the compositions of the invention.

FIGS. 1, 2, and 5 show typical dissolution curves for DORYX tablet measured under different pH conditions. FIG. 1 shows release data after 1 hour in 0.06N HCl, at approximately pH 1.2, typical stomach pH conditions. The initial release of the doxycyclinein DORYX is modest, reflecting the enteric coated delayed release nature of the product. However, at 20 minutes the doxycycline release rates starts to rise rapidly and after 60 minutes the release has reached virtually 100%. Similarly, for the release rate of the product at pH 4.5, after 60 minutes approximately 70% of the product has been released. In pH 5 conditions as might be expected, the release rate at 60 minutes is virtually 100%. An immediate release tablet formulation comprising doxycycline can be prepared by mixing doxycycline with a bulking agent such as microcrystalline cellulose, for example, AVIC$^{EL}$® (FMC Corp.) or EMCOC$^{EL}$® (Mendell Inc.); dicalcium phosphate, for example, EMCOM PRE$^{SS}$® (Mendell Inc.); calcium sulfate, for example, COMPAC-TR$^{OL}$® (Mendell Inc.); and starches, for example, STARCH 1500. Additionally, one can add a disintegrating agent, such as microcrystalline cellulose, starches, crospovidone, for example, POLYPLASDONE$^{XL}$® (International Specialty Products); sodium starch glycolate, for example, EXPLOT$^{AB}$® (Mendell Inc.); and croscarmellose sodium, for example, AC-DI-S$^{OL}$® (FMC Corp.). Antiadherants and glidants employed herein can include talc, cornstarch, silicon dioxide, sodium lauryl sulfate, colloidal silica dioxide, and metallic stearates.

Lubricants may be employed, such as magnesium stearate, calcium stearate, sodium stearate, stearic acid, sodium stearyl fumarate, sterotex, talc, waxes and the like.

Binding agents may be employed, such as polyvinyl pyrollidone, starch, methylcellulose, hydroxypropyl methylcellulose, carboxymethyl cellulose, and the like.

The immediate release formulations may be formed into a tablet using methods known in the art, including a wet granulation method and a direct compression method. The oral tablets are prepared using any suitable process known to the art. See, e.g., Remington's Pharmaceutical Sciences, 18th Edition, A. Gennaro, Ed., Mack Pub. Co. (Easton, Pa. 1990), Chapters 88-91, the entirety of which is hereby incorporated by reference. Typically, the active ingredient, which in embodiments is doxycycline (or salts and/or solvates thereof), is mixed with pharmaceutically acceptable excipients (e.g., the binders, lubricants, etc. listed above) and compressed into tablets.

In some embodiments, the dosage form of the present invention is prepared by a wet granulation technique or a direct compression method to form uniform granulates. If a wet granulation technique is used, the moist granulated mass can be dried and sized using a suitable screening device to provide a powder, which can then be filled into capsules or compressed into matrix tablets or caplets, as desired. In particular embodiments, the moist granulated mass is extruded, cut and then spheronized and dried to form pellets. These pellets are then coated with an optional stabilizing coating, and a sustained-release coating, and then filled into capsules.

In an embodiment, matrix tablets are prepared using the direct compression method. The direct compression method offers a number of potential advantages over a wet granulation method, particularly with respect to the relative ease of manufacture. In the direct compression method, at least one pharmaceutically active agent and the excipients or other ingredients are sieved through a stainless steel screen, such as a 40 mesh steel screen. The sieved materials are then charged to a suitable blender and blended for 10 minutes with an intensifier bar for three minutes. The blend is then compressed into tablets on a rotary press using appropriate tooling.

As aforementioned, immediate release formulations of tetracycline antibiotics suffer from a number of drawbacks, such as gastrointestinal irritation and nausea. Thus, although the present specification provides methods for producing such immediate release formulations, the following exemplary embodiments of sustained release tetracycline (e.g. doxycycline) formulations are advantageous over such immediate release formulations.

The sustained release formulations described herein exhibit a beneficial release profile that reduces or prevents nausea in patients administered the formulation. Furthermore, the sustained release formulations described in the present disclosure have a superior release profile compared to that of other doxycycline formulations.

In a particular aspect, the present invention provides for tablets or capsules comprising controlled release compositions of doxycycline. In various embodiments, the tablets or capsules can be prepared from, or be filled with, beads, particles or pellets containing doxycycline, in which the beads, particles or pellets can comprise a sustained-release matrix containing doxycycline, or the beads, particles pellets are coated with one or more layers of sustained release coating(s).

In specific embodiments, the sustained release formulations of the present invention comprise doxycycline-containing particles coated with a sustained release coating comprising an enteric polymer. In other specific embodiments, the sustained-release formulations of the present invention comprise doxycycline-containing particles coated with a sustained-release coating comprising a mixture of an enteric polymer and a water-soluble polymer. In still other embodiments, the sustained-release coating (e.g., a mixture of an enteric polymer and a water-soluble polymer, or solely an enteric polymer), further comprises a plasticizer.

In other embodiments, the pellets are coated with one layer of sustained-release coating (as described herein above), or two or more layers of sustained-release coating. Each of the sustained-release coatings can be the same or different.

Methods for making such controlled release pellets are set forth below. The pellets can be filled into capsules, for instance gelatin capsules, by conventional techniques. The pellets can also be incorporated into tablets, e.g. by compression using conventional techniques.

Controlled Release Pellets

In various embodiments, the sustained release preparations of the present disclosure will be formulated from a plurality of pellets.

In some embodiments, each pellet comprises a drug-containing core, coated with a sustained-release coating. In various aspects, the core comprises a tetracycline antibiotic. In a particular aspect, the core comprises doxycycline and the sustained release coating comprises an enteric polymer.

In some embodiments, a stabilizing coat is disposed between the core and the sustained release coating.

In one embodiment, a plurality of such pellets as described above may be provided in a capsule.

In alternative embodiments, a plurality of such pellets may be compressed, along with suitable optional tablet excipients, and provided as a tablet.

It is also possible for the dosage form to be a single coated core, large enough itself to be referred to as a tablet.

While suitable tableting excipients will be known to a person skilled in the art, proper formulation of the tablet usually involves balancing the need for content uniformity (namely, making sure the same number of pellets is present in each tablet and therefore the same amount of active ingredient is present in each tablet) and the amount of excipients required to protect the friable coating of the sustained release pellets. In this respect, if the number of pellets is too low, there may be problems with content uniformity, while if the number of pellets is too high there will not be enough tableting excipients to cushion the pellets during compression into a tablet and the modified release coating could be compromised. Therefore, the percentage of pellets in each tablet may be in the range of 20% to 40%, or in the range of 25% to 35%, or approximately 30% by weight of the total dosage weight.

Dosage forms (e.g. tablets or pellets suitable for filling into capsules) according to the present invention may further comprise excipients such as fillers, binders, disintegrants, and lubricants along with the active ingredient. Optionally, the dosage form (particularly tablets) may also contain other ingredients such as flavors, coloring agents, etc. The range of materials that are suitable for use as fillers, disintegrants, binders, lubricants, diluents, plasticizers, anti-caking agents, solubilizing agents, stabilizers, anti-oxidants, anti-adherents, preservatives, glidants, flavorants, sweeteners, and pigments will be well known to the person skilled in the art.

Suitable fillers include inert, relatively tasteless or pleasant tasting materials. A nonlimiting list of suitable fillers includes cellulose (e.g. microcrystalline cellulose), starch (e.g. corn starch), pregelatinized starch, modified starch, dibasic calcium phosphate dihydrate, calcium sulfate trihydrate, calcium sulfate dihydrate, calcium carbonate, dextrose, sucrose, lactose, mannitol, and sorbitol. Lactose monohydrate is used as filler in certain embodiments. In certain embodiments, the filler is at least one member selected from the group consisting of: lactose monohydrate, cellulose microcrystalline, corn starch, and combinations thereof.

A nonlimiting list of suitable disintegrants include cross-linked polymers such as crospovidone, croscarmellose sodium, etc., and modified starches such as sodium starch glycolate.

A nonlimiting list of suitable binders includes disaccharides such as sucrose and lactose, polysaccharides such as cellulose, starches, microcrystalline cellulose, modified celluloses such as hydroxypropyl cellulose, sugar alcohols such as xylitol, sorbitol, or maltitol, proteins such as gelatin, synthetic polymers such as polyvinyl pyrrolidone and polyethylene glycol, starches, such as potato starch, wheat starch, corn starch, and gums, such as gum tragacanth, acacia gum and gelatin.

A nonlimiting list of suitable lubricants includes magnesium stearate or stearic acid.

Plasticizers utilized in some embodiments include, but are not limited to, citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, dibutyrate, -dipropionate; tributyl phosphate, tributyrin; polyethylene glycol sorbitan monooleate (polysorbates such as Polysorbar 50); sorbitan monooleate. A combination of plasticizers may also be used. In aspects, the plasticizer for use with the cellulose polymer is polyethylene glycol, such as polyethylene glycol 600. In other aspects, the plasticizer for use with the enteric coating polymer is a combination of triethyl citrate and glycerol monostearate. In particular embodiments, the plasticizer comprises triethyl citrate (TEC).

It is also well known in the art that certain excipients may have multiple functions; e.g., function as fillers and binders.

In embodiments, lactose and/or starch are used as fillers in the dosage form. The total amount of lactose plus starch present in the dosage form can range between 50% to 95% w/w, based on the total weight of the tablet.

A suitable disintegrant for use in a dosage form of the present invention is crospovidone, and this may be present in a range of 0% to 15% w/w, based on the total weight of the tablet.

A suitable lubricant for use in a dosage form of the present invention is magnesium stearate and the lubricant may be present in a range of between 0.2% to 1.0% w/w, based on the total weight of the tablet.

Core of the Sustained Release Pellets

In other embodiments, the drug-containing core comprises active ingredient (e.g., doxycycline) mixed within and through the core. The core may be formed by any suitable method. For example, the core elements may be formed by layering the drug onto an inert core (e.g., a sugar bead or nonpareil, silica bead, etc., optionally in the presence of a binder to promote adhesion of the drug onto the inner core), extrusion, marumerisation, or rotogranulation. For example, the drug-containing core can comprise a mixture of the drug (e.g. doxycycline) and the filler or other excipient (e.g. microcrystalline cellulose) which are granulated (typically, wet granulated, but also dry granulated) to form (after drying, if necessary) either a "granulate" which are aggregated particles made up of drug and excipient particles adhered together. Alternatively, the drug and excipients can be wet granulated to form an extrudable mass which is extruded and cut into particles, and optionally spheronized to form drug-containing cores The active ingredient, in particular embodiments, is a tetracycline antibiotic (including salts, esters, and/or solvates thereof). In specific embodiments, the active ingredient is doxycycline. In some embodiments, the active ingredient is the monohydrate form of doxycycline. In further embodiments, the active ingredient is the hyclate salt form of doxycycline.

In embodiments, before coating with an optional stabilizing coat and the sustained release coating, the drug-containing cores have a diameter in the range of 50 microns to 2000 microns. Alternatively, if the drug is formulated into matrix tablets, the size of such tablets ranges from 5 mm to 20 mm.

It will be appreciated that the drug-containing cores may contain any suitable or required additives, such as excipients, fillers, or other ingredients.

In one embodiment, the core is formed by extrusion using an extruding solution. The core composition contains, in addition to the active ingredient, a binder.

In various embodiments, the binder is microcrystalline cellulose; however, powdered cellulose or any of the co-processed microcrystalline celluloses that contain additives such as silica, may be used. In embodiments, the amount of binder used ranges between about 6% to 45% by weight, based on the total weight of the core.

In embodiments, a wicking agent or water transport modifier may also be present in the core formulation. A wicking agent allows water to be transported throughout the core and aids in the complete release of active ingredient in the core. In certain aspects, the wicking agent is selected from lactose, starch, or sorbitol. In a particular embodiment, the wicking agent is lactose. The wicking agent may be present in an amount of from about 0% to 45% by weight, based on the total weight of the core.

Optionally, the core formulation may also include a lubricant, and a number of suitable lubricants will be known to the person skilled in the art. In a particular aspect, the lubricant is selected from sodium lauryl sulphate or magnesium stearate. In some aspects, the lubricant is present in an amount ranging from about 0% to 10% by weight, based on the total weight of the core.

The active ingredient (e.g., doxycycline) may be present in the core element in any suitable amount, and for instance may be provided in an amount from about 5% to 95% by weight, or from about 20% to 80% by weight, based on the total weight of the core element. In some embodiments, the amount of doxycycline (and salts and/or solvates thereof) is about 60% to about 80%, or about 70% to about 80%, or about 72% of the weight of the core element.

A person skilled in the art of making cores for pellets will be familiar with other materials that may be used to provide the same physical effects as the binder, the wicking agent, or the lubricant.

The active ingredient may be any suitable and desirable pharmaceutical, medicament, or chemical. For example, the active ingredient may be acid addition salts of doxycycline, tetracycline, oxytetracycline, minocycline, chlortetracycline, or demeclocycline. Any active ingredient that causes nausea or gastrointestinal irritation, but also has a narrow absorption window in the upper intestinal tract will benefit from the application of this disclosure.

In embodiments, the core comprises a tetracycline.

In other embodiments, the core comprises doxycycline.

In particular embodiments, the core element comprises the hyclate salt of doxycycline. In some aspects, the core element comprises the hyclate salt of doxycycline in amounts ranging from about: 1% to about 99% by weight, or 5% to 95% by weight, or from about 20% to 80% by weight, or about 50% to about 80% by weight, or about 60% to about 80% by weight, or about 70% to about 80% by weight or about 72% by weight based on the total weight of the core element.

Stabilizing Coating

The stabilizing coating is a physical barrier between the active ingredient (e.g. doxycycline) and the sustained release coating. The stabilizing coating may also be referred to as a tie coat, seal coat, or an intermediary layer.

The purpose of the stabilizing coating is to keep the active ingredient and the sustained release coating separated. In this respect, it is believed that the stabilizing coating slows migration of moisture or solvent between the modified release coating and the active ingredient. Whilst the stabilizing coating will keep the active ingredient separated from the sustained release coating during storage, the stabilizing coating will ideally not interfere significantly with the rate of release of the active ingredient, and therefore should be at least semi-permeable in aqueous media and may even be soluble. Indeed, the stabilizing coating is intended to keep migration of core materials to a minimum such that interaction with coating materials is reduced or prevented, whilst still allowing for release of the drug in an aqueous environment.

The stabilizing coating may thus be any suitable material which makes an inert barrier between the core (i.e. the active ingredient containing layer) and the modified release coating, and may be water soluble, water swellable, or water permeable polymeric or monomeric materials. Examples of such materials include, but are not limited to, hydroxypropylmethyl cellulose, hydroxypropyl cellulose, polyvinyl pyrrolidone, polyethylene glycol, or methacrylate based polymers (e.g. Eudragit® RS or Eudragit® RL).

In embodiments, the stabilizing coating includes a water-soluble polymer that does not interfere with the release of the active ingredient, and talc or another agent that performs the same function as talc. In various aspects, the water soluble polymer and talc may be present in the range of between 9 parts polymer to 1 part talc, through to 1 part polymer to 9 parts talc.

Controlled Release Coating

The controlled release coating may also be any suitable coating material, or combination of coating materials, that will provide the desired sustained release profile.

For example, coatings such as enteric coatings, semi-enteric coatings, delayed release coatings, or pulsed release coatings may be desired. In particular, a coating will be suitable if it provides an appropriate lag in active release prior to the rapid release at a rate essentially equivalent to immediate release of the active ingredient.

In particular, acid functional polymers such as hydroxypropylmethyl cellulose phthalate of varying grades (and also as an aqueous dispersion), methacrylate based polymers (e.g. Eudragit® L100-55 and Eudragit® L30D) and hydroxypropylmethyl cellulose acetate succinate, and other similar, pharmaceutically acceptable materials such as hydroxypropylmethyl cellulose acetate succinate, cellulose acetate succinate; cellulose acetate phthalate, hydroxypropylmethyl cellulose acetate succinate, cellulose acetate trimellitate, hydroxypropyl methyl cellulose phthalate, hydroxypropyl methyl cellulose acetate succinate, starch acetate phthalate, polyvinyl acetate phthalate, carboxymethyl cellulose, methyl cellulose phthalate, methyl cellulose succinate, methyl cellulose phthalate succinate, methyl cellulose phthalic acid half ester, and ethyl cellulose succinate.

It is also possible to use a mixture of enteric polymers to produce the modified release coating. It is also possible to use a mixture of enteric polymer with a water permeable, water swellable, or water-soluble material.

Suitable water-soluble or water permeable polymers include, but are not limited to, hydroxypropylmethyl cellulose, hydroxypropyl cellulose, polyvinyl pyrrolidone, polyethylene glycol, sodium alginate, and other similar, pharmaceutically acceptable materials, or mixtures thereof.

The controlled release coating may contain between 40% to 90% w/w enteric polymer. In some embodiments, the controlled release coating can also contain between 10% to 60% w/w water-soluble or water permeable polymers, based on the total weight of the controlled release coating. The controlled release coating may also contain 0% to 30% w/w of a plasticizer, based on the total weight of the controlled release coating.

In other embodiments, the controlled release coating contains about 80% to about 90% w/w of enteric polymer, optionally in combination with about 10% to about 20% w/w of a plasticizer. In particular embodiments, the controlled release coating contains about 84% w/w of enteric polymer, and optionally about 16% w/w of a plasticizer. In still other embodiments, the controlled release coating contains about 80% to about 90% w/w of enteric polymer and about 10% to about 20% w/w of water-soluble or water permeable polymer. In particular embodiments, the controlled release coating contains about 84% w/w of enteric polymer and about 16% w/w of water-soluble or water permeable polymer.

The "coating weight" of the controlled release coating refers to the amount of the coating, usually expressed as a weight percentage of the dried coating relative to the total weight of the pellet. The coating weight of the controlled release coating will vary depending on the delay desired and the polymer used, but generally will be between 5% w/w and 20% w/w.

The stabilizing coating and the controlled release coating may be applied to a core element in any suitable manner, such as by fluidized bed coating, including Würster coating, and rotacoating. In a particular aspect, both coatings will be applied by Würster coating.

Drying the pellet using any one of a number of drying techniques known in the art, such as oven drying or drying in a fluidized bed apparatus, may further improve stability.

Enteric Coatings

Controlled release preparations in accordance with the present disclosure will typically be such as to provide a delayed release of the active ingredient, with reference to the active ingredient's dissolution profile.

In this respect, where the controlled release is such as to provide a delayed release (generally referred to as a 'delayed release preparation') the composition is designed to slow the release of the active agent (e.g. doxycycline) in the stomach to minimize the side effects of the active agent that may be caused by its release in the stomach. Such side effects for tetracyclines, including doxycycline, include nausea and gastrointestinal irritation.

Most delayed release preparations aim for the drug to be released in the upper regions of the small intestines, for a number of reasons, as follows:

a) the drug is able to start working as soon as possible after ingestion without side effects caused by drug being released in the stomach;

b) the conditions in the upper small intestine are usually optimum for drug absorption; and c) to avoid acid degradation of the drug in the stomach.

By way of explanation, the stomach contents of healthy individuals who have eaten average meals usually have a residence time of 30 minutes to an hour and are at a pH in the stomach usually in the range of 1.0 to 3.0. The stomach contents then move to the intestines where the pH usually ranges from 4.0 to 7.0, where a rapid release of the active ingredient is desired to allow rapid and complete absorption of the active ingredient. There may be release of the drug in the stomach after a lag period, if the residence time is longer or the stomach conditions are different from usual, but the release will be at a much slower rate than an immediate release preparation, so the high localized concentrations that cause nausea and irritation do not occur.

Therefore, in various embodiments, a delayed or controlled release profile exhibits minimal release of the active ingredient at the low pH levels characteristic of the stomach, over a period of approximately 60 minutes, but when exposed to a higher pH, e.g. at least about 4.5, essentially 100% of the active ingredient is released within about 60 minutes.

The release profile of the compositions of the present invention differ from those of prior art compositions. At a pH of about 1.2, the compositions of the present invention exhibit minimal release of the drug (e.g., doxycycline), for example less than about 15% release after 60 minutes, whereas conventional compositions (such as Doryx) release essentially 100% of the drug under the same conditions after 60 minutes. As a result, the compositions of the present invention release substantially lower amounts of drug in the stomach of a patient (after ingestion), and thus reduce the incidence of undesirable side effects such as nausea and gastrointestinal irritation.

The release profile of the compositions of the present invention also differ from that of prior art compositions (e.g., DORYX) at the higher pH levels typical of the upper intestinal tract. For example, at pH 4.5, compositions of the present invention (e.g., comprising doxycycline as the active agent) release less than about 5% of the drug after 30 minutes, about 10 to about 30% of the drug after 60 minutes, about 20 to about 50% of the drug after 90 minutes, about 30 to about 60% of the drug after 120 minutes, and about 50 to about 70% of the drug after 180 minutes. In contrast, comparable conventional compositions (e.g. DORYX) release about 50%, about 70%, about 80%, about 85%, and about 90% of the drug at the same time intervals. At pH 5, compositions of the present invention (e.g., comprising doxycycline as the active agent) release about 45% to about 50% of the drug after 10 minutes, about 55% to about 65% of the drug at 20 minutes, about 65 to about 70% of the drug at 30 minutes, about 70% to about 75% of the drug at 45 minutes, and about 75 to about 80% of the drug at 60 minutes. In contrast, comparable conventional compositions (e.g. Doryx) release about 40% of the drug at 10 minutes, about 70% of the drug in 20 minutes, about 90% of the drug at 30 minutes, and about 100% after about 45 minutes.

The lower levels of (e.g., doxycycline) of the compositions of the present invention at pH of about 4.5 or 5 is indicative of the pH environment experienced by the drug formulation as it transitions from the pH levels of the stomach into the pH levels of the intestine. The compositions of the present invention show appreciably less release at these pH levels compared to conventional compositions, and therefore reduce nausea and gastrointestinal irritation in the patient. In particular, the lower release rates at the 'transitional' pH of about 4.5, compared to prior art formulations, ensures that the drug (e.g., doxycycline) will not release as it transits out of stomach, but that the release will be delayed until it is in the GI tract, which is believed to contribute to reduced side effects.

In practice, it is difficult to prepare formulations that release no active ingredient at stomach pH levels, but provide complete release of the active ingredient at pH levels found in the upper intestinal tract. Accordingly, suitable formulations release less than about 15% of the active ingredient at a pH of about 1.2 after 60 minutes, and at least 90% of the active ingredient is released after 4-5 hours at a pH of at least 4.5 in in vitro tests such as USP <711>. In some embodiments, suitable formulations release less than about 10% of the active ingredient at a pH of about 1.2 after 60 minutes.

The ability of the compositions of the disclosure to release less than 10% of the active ingredient during the initial 60 minutes of exposure to low pH (e.g. pH of 1.0 to 3.0) is an improvement over conventional compositions, particularly conventional tetracycline compositions because it provides for lower levels of nausea and gastric irritation, while still providing sufficient exposure to the drug to provide the desired clinical effect. Conventional approaches to delay drug release in the stomach (e.g. adding thick enteric coatings or conventional controlled release coatings) may be useful in reducing release of the drug in the stomach, but can delay or retard absorption of the drug, thereby limiting its therapeutic benefits. The compositions of the present invention, however, provide minimal release of the drug in the stomach while maintaining high levels of clinical efficacy.

In one aspect of the invention, no more than 10% of the active ingredient is released at a pH of about 1.2 by 60 minutes and at least 80% of the active ingredient is released at a pH of at least 4.5 by about 5 hours when tested using USP <711> conditions.

In other embodiments, the compositions of the present invention have a release profile at a pH of about 1.2 (e.g., 0.06N HCl) when tested using USP <711> conditions, substantially identical to the curves labeled "Pellet A" or "Pellet B" of FIG. 1. In still other embodiments, the compositions of the present invention have a release profile at a pH of about 4.5 (phosphate buffer) when tested using USP <711> conditions, substantially identical to the curves labeled "Pellet A" or "Pellet B" of FIG. 2.

For the purposes of in vitro testing, a release or dissolution profile may be determined at pH 1.2 using a 0.06 N hydrochloric acid solution, and at pH 4.5 using a phosphate buffer using USP <711> test conditions.

The release profiles described above for the compositions of the present invention are preferred for some pharmaceutical active ingredients such as tetracycline antibiotics (e.g. doxycycline), or for any drug that can cause nausea or gastrointestinal irritation, but that has a narrow absorption window in the upper intestinal tract. For such drugs, it is preferable to limit release in the stomach, but to provide sufficient release within the narrow absorption window in the upper intestinal tract so as to provide clinically effective levels of the drug. In this manner, substantially identical exposure (i.e., AUC) can be provided by the compositions of the present invention relative to conventional formulations, which provides the desired clinical efficacy, but reduced release of the drug at low pH (i.e. in the stomach) reduces side effects such as nausea and gastrointestinal irritation.

For example, bisphosphonates are known to cause gastrointestinal ulceration at higher doses, opioid analgesics are known to cause nausea, and very basic drugs can be neutralized by the acidic conditions of the stomach, precipitate and not be absorbed. Additionally, other reactions may take place causing the activity of the drug to be lost.

Pharmaceutical Compositions

In certain embodiments, the pharmaceutical composition comprises the core containing the active therapeutic agent, a stabilizing coating, and a controlled release coating comprising an enteric polymer.

In other embodiments, the pharmaceutical composition comprises the core containing the active therapeutic agent, a stabilizing coating, a controlled release coating comprising an enteric polymer, and a pharmaceutically acceptable carrier.

Capsules Containing the Controlled Release Pellets

In particular embodiments, the pharmaceutical compositions of the present invention comprise a capsule, wherein said capsule contains a plurality of pellets each comprising: a core containing the active therapeutic agent, an optional stabilizing coating, and a controlled release coating comprising an enteric polymer as described herein.

In other embodiments, the controlled release pellet comprises a core containing doxycycline hyclate. In other embodiments, the controlled release pellet comprises a core containing the monohydrate form of doxycycline.

In embodiments, the capsule comprises a total amount of doxycycline hyclate of about 25 mg per capsule, or about 50 mg per capsule, or about 60 mg per capsule, or about 75 mg per capsule, or about 90 mg per capsule, or about 100 mg per capsule, or about 120 mg per capsule, or about 150 mg per capsule, or about 200 mg per capsule, or more.

In embodiments, the capsule comprises a total amount of doxycycline hyclate of about 50 mg per capsule±about 10 mg, about 60 mg per capsule±about 10 mg, about 75 mg per capsule±about 10 mg, about 90 mg per capsule±about 10 mg, about 100 mg per capsule±about 10 mg, about 120 mg per capsule±about 10 mg, about 150 mg per capsule±about 10 mg, or about 200 mg per capsule±about 10 mg.

In embodiments, the capsule comprises a total amount of doxycycline hyclate of about 50 mg per capsule±about 5 mg, about 60 mg per capsule±about 5 mg, about 75 mg per capsule±about 5 mg, about 90 mg per capsule±about 5 mg, about 100 mg per capsule±about 5 mg, about 120 mg per capsule±about 5 mg, about 150 mg per capsule±about 5 mg, or about 200 mg per capsule±about 5 mg.

In embodiments, the capsule comprises a total amount of doxycycline hyclate of about 50 mg per capsule, about 60 mg per capsule, about 75 mg per capsule, about 90 mg per capsule, about 100 mg per capsule, about 120 mg per capsule, about 150 mg per capsule, or about 200 mg per capsule.

Tablets Containing the Controlled Release Pellets

In some embodiments, the pharmaceutical composition comprises a tablet, wherein said tablet contains at least one pellet comprising: a core containing the active therapeutic agent, an optional stabilizing coating, and a modified release coating comprising an enteric coating.

In embodiments, the controlled release pellet comprises a core containing doxycycline hyclate.

In embodiments, the tablet comprises a total amount of doxycycline hyclate of about 25 mg per tablet, about 50 mg per tablet, about 60 mg per tablet, about 75 mg per tablet, about 90 mg per tablet, about 100 mg per tablet, about 120 mg per tablet, about 150 mg per tablet, about 200 mg per tablet, or more.

In embodiments, the tablet comprises a total amount of doxycycline hyclate of about 50 mg per tablet±about 10 mg, about 60 mg per tablet±about 10 mg, about 75 mg per tablet±about 10 mg, about 90 mg per tablet±about 10 mg, about 100 mg per tablet±about 10 mg, about 120 mg per tablet±about 10 mg, about 150 mg per tablet±about 10 mg, or about 200 mg per tablet±about 10 mg.

In embodiments, the tablet comprises a total amount of doxycycline hyclate of about 50 mg per tablet±about 5 mg, about 60 mg per tablet±about 5 mg, about 75 mg per tablet±about 5 mg, about 90 mg per tablet±about 5 mg, about 100 mg per tablet±about 5 mg, about 120 mg per tablet±about 5 mg, about 150 mg per tablet±about 5 mg, or about 200 mg per tablet±about 5 mg.

In embodiments, the tablet comprises a total amount of doxycycline hyclate of about 50 mg per tablet, about 60 mg per tablet, about 75 mg per tablet, about 90 mg per tablet, about 100 mg per tablet, about 120 mg per tablet, about 150 mg per tablet, or about 200 mg per tablet.

Course of Treatment

The controlled release formulations comprising doxycycline can be utilized to treat acne in certain embodiments.

The controlled release pharmaceutical compositions comprising doxycycline may be administered once per day, twice per day, three times per day, or more, to a patient in need thereof. In some embodiments, the patient suffers from mild acne. In some embodiments, the patient suffers from severe acne.

In a particular embodiment, a patient suffering from acne is administered one capsule or tablet comprising controlled release doxycycline. In more particular embodiments, each controlled release pellet of the capsule comprises: a doxycycline-containing core, an optional stabilizing coating, and a controlled release coating. The tablet or capsule may comprise about 60 mg doxycycline, about 75 mg doxycycline, about 90 mg doxycycline, about 100 mg doxycycline, about 120 mg doxycycline, about 150 mg doxycycline, or about 200 mg doxycycline, and may be administered once or twice per day.

In particular embodiments, a patient is administered one tablet or capsule comprising about 60 or 120 mg doxycycline every 12 hours for the first 24 hours (i.e. total of 120 or 240 mg doxycycline in first 24 hours), which is followed by a maintenance dose of one tablet or capsule comprising about 120 mg doxycycline once daily. However, variations in this mode of treatment may be contemplated by physicians.

In embodiments, the adult dosage of oral doxycycline compositions, as taught herein, are to be administered in the amount of 240 mg on the first day of treatment (administered 120 mg every 12 hours), followed by a maintenance dose of 120 mg daily. The maintenance dose may be administered as a single dose or as 60 mg every 12 hours. In the management of more severe infections (particularly chronic infections of the urinary tract), 120 mg every 12 hours can be utilized.

In embodiments, the pediatric (above 8 years of age) dosage of oral doxycycline compositions, as taught herein, are to be administered according to a dosage schedule for children weighing 45 kg or less at 4.4 mg/kg of body weight divided into two doses on the first day of treatment, followed by 2.2 mg/kg of body weight given as a single daily dose or divided into two doses on subsequent days. For more severe infections up to 4.4 mg/kg of body weight may be used. For children over 45 kg, the usual adult dose may be used.

The compositions of the disclosure are active against at least the following organisms: (1) Gram-Negative Bacteria including: *Neisseria gonorrhoeae; Calymmatobacterium granulomatis; Haemophilus ducreyi; Haemophilus influenza; Yersinia pestis* (formerly *Pasteurella pestis*); *Francisella tularensis* (formerly *Pasteurella tularensis*); *Vibrio cholerae* (formerly *Vibrio comma*); *Bartonella bacilliformis; Brucella* species; Because many strains of the following groups of gram-negative microorganisms have been shown to be resistant to tetracyclines, culture and susceptibility testing are recommended: *Escherichia coli; Klebsiella* species; *Enterobacter aerogenes; Shigella* species; *Acinetobacter* species (formerly *Mima* species and *Herellea* species); (2) Gram-Positive Bacteria including: *Streptococcus pyogenes; Streptococcus pneumonia; Enterococcus* group (*Streptococcus faecalis* and *Streptococcus faecium*); and Alpha-hemolytic streptococci (viridans group) (because many strains of the aforementioned groups of gram-positive microorganisms have been shown to be resistant to tetracycline, culture and susceptibility testing are recommended, as up to 44 percent of strains of *Streptococcus pyogenes* and 74 percent of *Streptococcus faecalis* have been found to be resistant to tetracycline drugs, therefore, tetracycline should not be used for streptococcal disease unless the organism has been demonstrated to be susceptible); (3) Other Microorganisms including: *Rickettsiae; Chlamydia psittaci; Chlamydia trachomatis; Mycoplasma pneumonia; Ureaplasma urealyticum; Borrelia recurrentis; Treponema pallidum; Treponema pertenue; Clostridium* species; *Fusobacterium fusiforme; Actinomyces* species; *Bacillus anthracis*; Propionibacterium acnes; *Entamoeba* species; *Balantidium coli; Plasmodium falciparum*; Doxycycline has been found to be active against the asexual erythrocytic forms of; *Plasmodium falciparum* but not against the gametocytes of *P. falciparum*. The precise mechanism of action of the drug is not known.

Doxycycline is indicated for the treatment of the following infections: Rocky Mountain spotted fever, typhus fever and the typhus group, Q fever, rickettsialpox, and tick fevers caused by Rickettsiae; Respiratory tract infections caused by *Mycoplasma pneumonia*; Lymphogranuloma venereum caused by *Chlamydia trachomatis*; Psittacosis (ornithosis) caused by *Chlamydia psittaci*; Trachoma caused by *Chlamydia trachomatis*, although the infectious agent is not always eliminated as judged by immunofluorescence; Inclusion conjunctivitis caused by *Chlamydia trachomatis*; Uncomplicated urethral, endocervical or rectal infections in adults caused by *Chlamydia trachomatis*; Nongonococcal urethritis caused by *Ureaplasma urealyticum*; Relapsing fever due to *Borrelia recurrentis*. Chancroid caused by Haemophilus ducreyi; Plague due to *Yersinia pestis* (formerly *Pasteurella pestis*); Tularemia due to *Francisella tularensis* (formerly *Pasteurella tularensis*); Cholera caused by *Vibrio cholerae* (formerly *Vibrio comma*); *Campylobacter fetus* infections caused by *Campylobacter fetus* (formerly *Vibrio fetus*); Brucellosis due to *Brucella species* (in conjunction with streptomycin); Bartonellosis due to *Bartonella bacilliformis*; Granuloma inguinale caused by *Calymmatobacterium granulomatis*; Doxycycline is indicated for treatment of infections caused by the following gram negative microorganisms, when bacteriological testing indicates appropriate susceptibility to the drug: *Escherichia coli; Enterobacter aerogenes* (formerly *Aerobacter aerogenes*); *Shigella* species; *Acinetobacter* species (formerly *Mima* species and *Herellea* species); Respiratory tract infections caused by *Haemophilus influenza*; Respiratory tract and urinary tract infections caused by *Klebsiella* species; Doxycycline is indicated for treatment of infections caused by the following gram positive microorganisms when bacteriological testing indicates appropriate susceptibility to the drug: Upper respiratory infections caused by *Streptococcus pneumoniae* (formerly *Diplococcus Pneumoniae*); Anthrax due to *Bacillus anthracis*, including inhalational anthrax (post-exposure): to reduce the incidence or progression of disease following exposure to aerosolized *Bacillus anthracis*; When penicillin is contraindicated, doxycycline is an alternative drug in the treatment of the following infections: Uncomplicated gonorrhea caused by *Neisseria gonorrhoeae*; Syphilis caused by *Treponema pallidum*; Yaws caused by *Treponema pertenue*; Listeriosis due to *Listeria monocytogenes*; Vincent's infection caused by *Fusobacterium fusiforme*; Actinomycosis caused by *Actinomyces israelii*; Infections caused by *Clostridium* species; In acute intestinal amebiasis, doxycycline may be a useful adjunct to amebicides; In severe acne, doxycycline may be useful adjunctive therapy; Prophylaxis: Doxycycline is indicated for the prophylaxis of malaria due to *Plasmodium falciparum* in short-term travelers (<4 months) to areas with chloroquine and/or pyrimethaminesulfadoxine resistant strains.

The following non-limiting Examples illustrate certain aspects of the present disclosure.

EXAMPLES

Example 1

Preparation of Controlled Release Doxycycline Hyclate Pellets Core Preparation

The core is formed in a wet granulation process using a saturated solution of sodium chloride and in a high shear mixer.

The mixture is then extruded using a screen size of between 0.4 and 1.5 mm. The extrudate is then marumerised to produce rounded core elements. The core elements are dried in a fluidized bed or an oven.

Stabilizing Coat Application

A stabilizing coat is applied to the core using a fluidized bed coating process.

The stabilizing coat contains hydroxypropylmethyl cellulose and talc in a 2:1 mixture.

The desired polymer coat weight (i.e. the weight of the polymer only, not including the talc) is between 3% and 5% of the total weight of the core element and the stabilizing coat.

The polymer coat weight will vary due to a number of factors, such as the efficiency of the coating process, the batch of raw materials, etc.

Modified Release Coat Application

The modified release coating is applied to the stabilizing coated core using a fluidized bed coating process to form pellets.

The desired polymer coat weight is 15% of the total weight of the pellet.

Table 1, below, provides examples of two controlled release doxycycline hyclate formulations derived according to the above procedure. Table 1 also provides the formulation components for a commercially available doxycycline hyclate formulation (DORYX) for comparison.

TABLE 1

Formulation of a Modified Release Coating Layer of a Controlled Release Doxycycline Pellet

| Wt % in modified release coating | DORYX 75 mg Pellet | Pellet Formulation A | Pellet Formulation B |
|---|---|---|---|
| HP 50 (hydroxyl propyl methyl cellulose phthalate) | 67 | 84 | 84 |
| HPMC (hydroxyl propyl methyl cellulose) | 16 | 16 | 0 |
| TEC (tri ethyl citrate) | 17 | 0 | 16 |
| Theoretical Polymer coat weight as % of total weight of the pellet | 15 | 28 | 11 |

The in vitro release of the pellets was tested using USP XXIV 2000—Apparatus 1 (baskets). See, e.g., Riaz Uddin, Nadia Saffoon, and Kumar Bishwajit Sutradhar, "Dissolution and Dissolution Apparatus: A Review," Int. J. Cur. Biomed. Phar. Res., 2011, Vol. 1(4), pgs. 201-207.

The dissolution profiles of the formulations are contained below.

The aforementioned pellet formulations of doxycycline hyclate can be packed into capsules and also formulated as tablets. In the following dissolution experiments, the pellets were loaded into capsules.

Example 2

Dissolution Profiles of Control (DORYX), Pellet A Formulation, & Pellet B Formulation Acidic Dissolution Profile The acid environment dissolution profile of pellet A and B's formulation can be seen in FIG. 1.

As can be seen in FIG. 1, the formulations of pellet A and B release less than 10% of the doxycycline hyclate in an acid environment (pH of approximately 1.2) after 60 minutes of exposure under standard USP conditions.

The slow rate of release of doxycycline, in a pH of approximately 1.2, exhibited by the pellet formulations according to the disclosure is in stark contrast to the dissolution profile of the commercially available DORYX.

As can be seen in FIG. 1, the DORYX tablet released approximately 98%-100% of the doxycycline hyclate at 60 minutes.

Thus, the controlled release doxycycline formulations of the disclosure exhibit a beneficial and superior dissolution profile in acidic conditions, as compared to a commercially available doxycycline formulation.

Elevated pH Dissolution Profile

The dissolution profile of pellet A and B formulations at elevated pH can be seen in FIG. 2.

As can be seen in FIG. 2, the formulation of pellet A releases greater than about 25% of the doxycycline hyclate in a basic environment (pH of approximately 4.5) after 60 minutes of exposure under standard USP conditions.

Also, as can be seen in FIG. 2, the formulation of pellet B releases less than about 10% of the doxycycline hyclate in a basic environment (pH of approximately 4.5) after 60 minutes of exposure under standard USP conditions. Thus, the formulation of pellet B releases less than 10% of active ingredient in both an acidic and basic environment at 60 minutes.

The slow rate of release of doxycycline, in a pH of approximately 4.5, exhibited by the pellet formulations according to the disclosure is in stark contrast to the dissolution profile of the commercially available DORYX.

As can be seen in FIG. 2, the DORYX tablet released approximately 70% of the doxycycline hyclate at 60 minutes in a pH of 4.5.

Thus, the controlled release doxycycline formulations of the disclosure exhibit a beneficial and superior dissolution profile in basic conditions, as compared to a commercially available doxycycline formulation.

Example 3

Clinical Data

The aforementioned controlled release pellet formulations (A and B) were loaded into capsules and administered to 10 test subjects to obtain in vivo data.

It is also contemplated that pellet formulations A and B may be formulated into tablets.

After all 10 completed subjects were analyzed; the following Geometric Mean Ratio (GMR) and Intra-Subject Coefficient of Variation (CV) were obtained for the two Test Formulations.

TABLE 2

In Vitro Pharmacokinetics Data

| Formulation | Parameter | GMR (%) | CV (%) |
|---|---|---|---|
| Pellet A | $AUC_{0-\infty}$ | 89.64 | 17.24 |
| | $AUC_{0-t}$ | 89.58 | 17.71 |
| | $C_{max}$ | 88.08 | 19.87 |
| Pellet B | $AUC_{0-\infty}$ | 106.90 | 17.24 |
| | $AUC_{0-t}$ | 106.37 | 17.71 |
| | $C_{max}$ | 103.73 | 19.87 |

Figure 3:
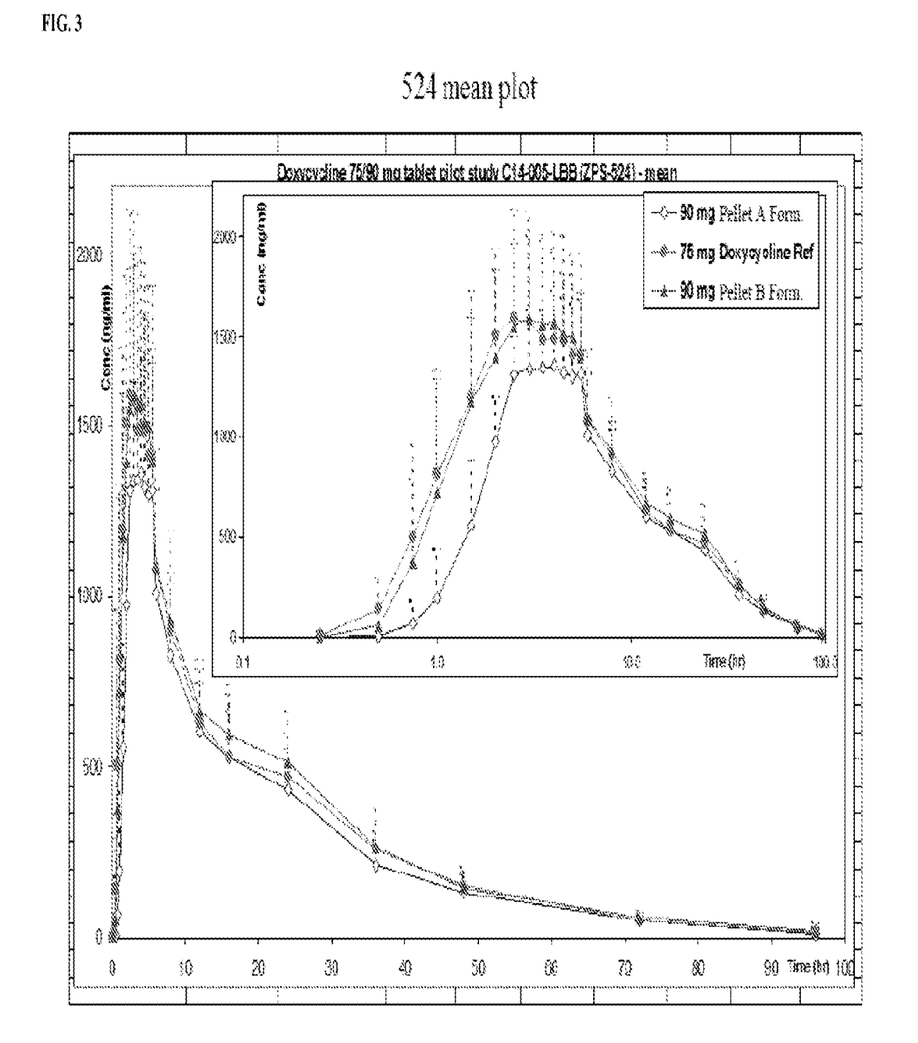
FIG. 3 is a graph of the mean concentration of doxycycline present in the plasma of subjects treated with a capsule comprising controlled release doxycycline pellet formulations (A or B) compared to a control doxycycline formulation.
Figure 4:
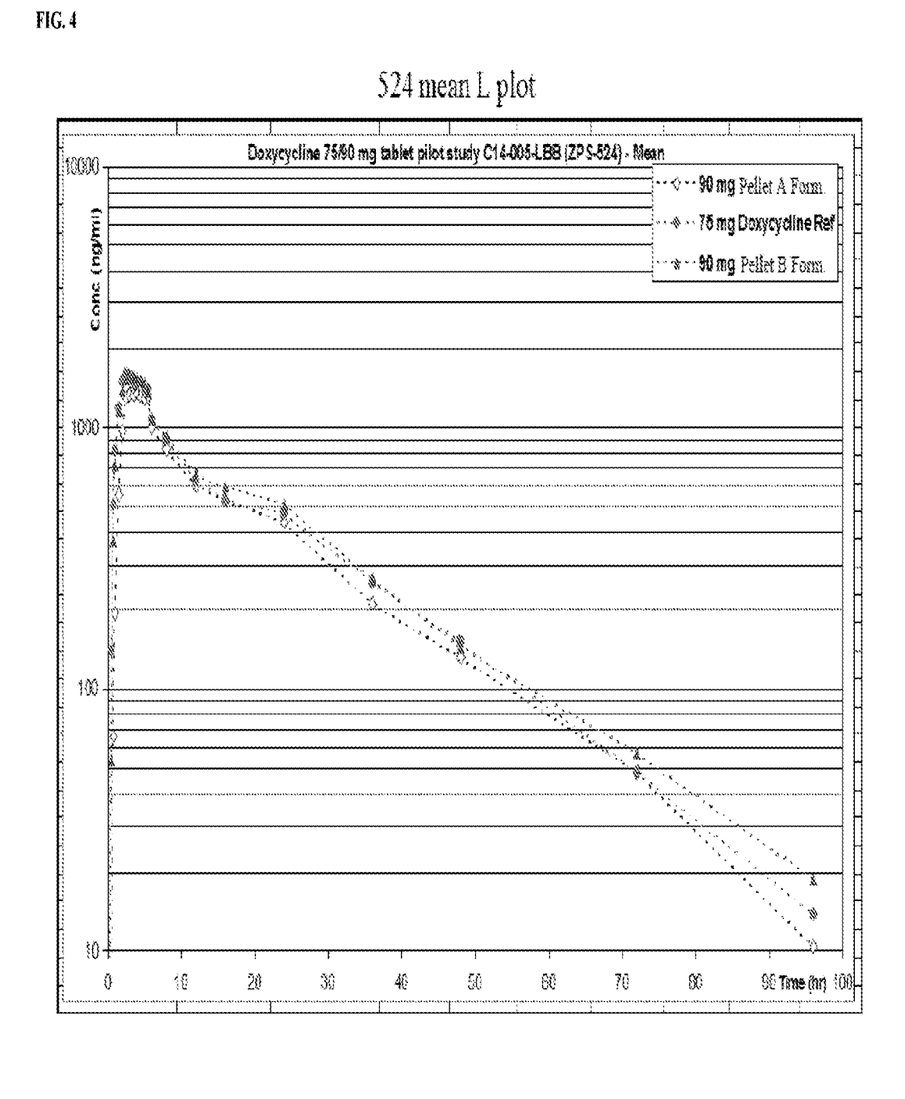
FIG. 4 is a graph of the mean logarithmic concentration of doxycycline present in the plasma of subjects treated with a capsule comprising controlled release doxycycline pellet formulations (A or B) compared to a control doxycycline formulation.

Further, FIG. 3 and FIG. 4 illustrate the concentration of active substance in ng/mL of the two tested pellet A and pellet B formulations as compared to a doxycycline (DORYX) control.

As shown in FIG. 3, 90 mg controlled release pellet formulations (A and B) of the present invention have average $AUC_{0-t}$ values (ng·hr/ml) which differ from that of conventional 75 mg doxycycline formulations (e.g., DORYX) during the initial two to three hours after administration. However, $AUC_{0-\infty}$ values for these compositions are essentially identical (i.e., bioequivalent) to that of the conventional DORYX composition. $AUC_{0-t}$ values at various time points for pellets A and B, compared to DORYX are shown below in Table 3.

TABLE 3

$AUC_{0-t}$ vs. TIME

| Time post administration (hours) | $AUC_{0-t}$ Doryx | $AUC_{0-t}$ Pellet A | $AUC_{0-t}$ Pellet B |
|---|---|---|---|
| 0.25 | 1 | 0 | 0 |
| 0.5 | 19 | 1 | 6 |
| 0.75 | 100 | 9 | 55 |
| 1 | 271 | 42 | 179 |
| 1.5 | 781 | 235 | 616 |
| 2 | 1,448 | 614 | 1,220 |
| 2.5 | 2,202 | 1,181 | 1,912 |
| 3 | 2,965 | 1,843 | 2,665 |
| 3.5 | 3,719 | 2,513 | 3,437 |
| 4 | 4,436 | 3,188 | 4,184 |
| 4.5 | 5,153 | 3,858 | 4,946 |
| 5 | 5,856 | 4,513 | 5,696 |
| 5.5 | 6,539 | 5,166 | 6,416 |
| 6 | 7,142 | 5,746 | 7,015 |
| 8 | 9,063 | 7,581 | 9,008 |
| 12 | 12,039 | 10,440 | 12,168 |
| 16 | 14,304 | 12,700 | 14,683 |
| 24 | 18,202 | 16,578 | 19,086 |
| 36 | 21,963 | 20,128 | 23,147 |
| 48 | 24,775 | 22,468 | 26,110 |
| 72 | 27,160 | 24,678 | 28,650 |
| 96 | 27,748 | 25,137 | 29,369 |

A larger follow-up study is being conducted. The following sample sizes, in Table 3, are required based on the above GMR and CV.

TABLE 4

Sample Size of Follow-up Pharmacokinetic Study

| Formulation | Parameter | Sample Size |
|---|---|---|
| Pellet A | $AUC_{0-\infty}$ | 30 |
| | $AUC_{0-t}$ | 32 |
| | Cmax | 56 |
| Pellet B | $AUC_{0-\infty}$ | 18 |
| | $AUC_{0-t}$ | 18 |
| | Cmax | 16 |

Example 4

Preparation of Controlled Release Doxycycline Monohydrate Pellets

Doxycycline is can be prepared as the hyclate salt, as described above. However, the monohydrate form of doxycycline is also available.

Currently, the monohydrate form of doxycycline is only commercially available as an immediate release form.

The monohydrate form of doxycycline may be safer to use than the hyclate salt, and hence a delayed release formulation of this product would provide meaningful benefits for patients.

However, doxycycline monohydrate does not behave in the same way as the hyclate product and presents challenges in formulation.

The present disclosure provides a controlled release formulation of doxycycline monohydrate, by providing a standard core that comprises the doxycycline monohydrate that is coated with the DORYX modified released coating.

Further modified release coating formulations are contemplated by the disclosure to achieve various dissolution profiles for the controlled release doxycycline monohydrate product.

A shown in FIG. 5, the monohydrate salt is very soluble at lower pH's and releases readily in acid, but is not very soluble at pH above 3, leading to low release rates overall.

While this disclosure has been described with respect to various specific examples and embodiments, it is to be understood that the disclosure is not limited thereto and that it can be variously practiced within the scope of the recited claims.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A dosage form comprising a plurality of modified release doxycycline pellets, wherein each doxycycline pellet comprises:
    doxycycline; and
    a controlled release polymer composition disposed over the doxycycline, wherein said dosage form comprises 60, 90, or 120 mg of doxycycline and maintains doxycycline release levels measured under USP <711> conditions at pH 5 that provide a clinically effective plasma level of doxycycline.

2. The dosage form of claim 1, wherein when the amount of doxycycline of said dosage form is 60 mg, after administration of a single dose under fasting conditions to a patient in need thereof, the average $C_{max}$ is about 80% to about 125% of about 625-1600 ng/ml;
    or
    wherein when the amount of doxycycline of said dosage form is 90 mg, after administration of a single dose under fasting conditions to a patient in need thereof, the average $C_{max}$ is about 80% to about 125% of about 940-2400 ng/ml;
    or
    wherein when the amount of doxycycline of said dosage form is 120 mg, after administration of a single dose under fasting conditions to a patient in need thereof, the average $C_{max}$ is about 80% to about 125% of about 1250-3200 ng/ml.

3. The dosage form of claim 1, wherein when the amount of doxycycline of said dosage form is 60 mg, after administration of a single dose to a patient in need thereof, the average $AUC_{0-\infty}$ is about 80% to about 125% of about 10000-24000 ng·hr/ml; or
    wherein when the amount of doxycycline of said dosage form is 90 mg, after administration of a single dose to a patient in need thereof, the average $AUC_{0-\infty}$ is about 80% to about 125% of about 15000-36500 ng·hr/ml; or
    wherein when the amount of doxycycline of said dosage form is 120 mg, after administration of a single dose to a patient in need thereof, the average $AUC_{0-\infty}$ is about 80% to about 125% of about 20000-48500 ng·hr/ml.

4. The dosage form of claim 2, wherein when the amount of doxycycline of said dosage form is 60 mg, after administration of a single dose to a patient in need thereof, the average $AUC_{0-\infty}$ is about 80% to about 125% of about 10000-24000 ng·hr/ml; or
    wherein when the amount of doxycycline of said dosage form is 90 mg, after administration of a single dose to a patient in need thereof, the average $AUC_{0-\infty}$ is about 80% to about 125% of about 15000-36500 ng·hr/ml; or
    wherein when the amount of doxycycline of said dosage form is 120 mg, after administration of a single dose to a patient in need thereof, the average $AUC_{0-\infty}$ is about 80% to about 125% of about 20000-48500 ng·hr/ml.

5. The dosage form of claim 1, wherein the release of doxycycline at pH 5 measured under USP <711> conditions is at least one of the following:
    about 45% to about 50% after 10 minutes;
    about 55% to about 65% at 20 minutes;
    about 65% to about 70% at 30 minutes;
    about 70% to about 75% at 45 minutes; and
    about 75% to about 80% at 60 minutes.

6. The dosage form of claim 1, wherein the dosage form maintains release levels measured under USP <711> conditions that are low at pH values up to pH 4.5.

7. The dosage form of claim 2, wherein the dosage form maintains release levels measured under USP <711> conditions that are low at pH values up to pH 4.5.

8. The dosage form of claim 3, wherein the dosage form maintains release levels measured under USP <711> conditions that are low at pH values up to pH 4.5.

9. The dosage form of claim 4, wherein the dosage form maintains release levels measured under USP <711> conditions that are low at pH values up to pH 4.5.

10. The dosage form of claim 5, wherein the release of doxycycline at pH 5 measured under USP <711> conditions is at least two of the following:
    about 45% to about 50% after 10 minutes;
    about 55% to about 65% at 20 minutes;
    about 65% to about 70% at 30 minutes;
    about 70% to about 75% at 45 minutes; and
    about 75% to about 80% at 60 minutes.

11. The dosage form of claim 5, wherein the release of doxycycline at pH 5 measured under USP <711> conditions is at least three of the following:
    about 45% to about 50% after 10 minutes;
    about 55% to about 65% at 20 minutes;
    about 65% to about 70% at 30 minutes;
    about 70% to about 75% at 45 minutes; and
    about 75% to about 80% at 60 minutes.

12. The dosage form of claim 5, wherein the release of doxycycline at pH 5 measured under USP <711> conditions is at least four of the following:
    about 45% to about 50% after 10 minutes;
    about 55% to about 65% at 20 minutes;
    about 65% to about 70% at 30 minutes;
    about 70% to about 75% at 45 minutes; and
    about 75% to about 80% at 60 minutes.

13. The dosage form of claim 5, wherein the release of doxycycline at pH 5 measured under USP <711> conditions is:
    about 45% to about 50% after 10 minutes;
    about 55% to about 65% at 20 minutes;
    about 65% to about 70% at 30 minutes;
    about 70% to about 75% at 45 minutes; and
    about 75% to about 80% at 60 minutes.

14. The dosage form of claim 1, wherein the doxycycline pellets comprise a doxycycline-containing core, and the controlled release polymer composition is disposed as a layer over the core.

15. The dosage form of claim 14, wherein the controlled release polymer composition comprises a blend of an enteric polymer and a water soluble polymer.

16. The dosage form of claim 15, wherein the controlled release polymer composition further comprises a plasticizer.

17. The dosage form of claim 16, wherein the controlled release polymer composition consists essentially of a blend of an enteric polymer, a water soluble polymer, and a plasticizer.

18. The dosage form of claim 14, further comprising a stabilizing coating disposed between the core and the controlled release polymer composition layer.

19. A method of treating a skin condition in a patient, comprising orally administering the dosage form of claim 1 to a patient in need thereof.

20. A method of treating a skin condition in a patient, comprising orally administering the dosage form of claim 14 to a patient in need thereof.

21. The method of claim 19, wherein said skin condition is at least one condition selected from the group consisting of: a skin infection, rosacea, acne, papules, pustules, open comedo, closed comedo, or a combination thereof.

22. The method of claim 20, wherein said skin condition is at least one condition selected from the group consisting of: a skin infection, rosacea, acne, papules, pustules, open comedo, closed comedo, or a combination thereof.

23. The method of claim 19, wherein said administering is once-per-day.

24. The method of claim 20, wherein said administering is once-per-day.

25. The dosage form of claim 1, wherein the amount of doxycycline of said dosage form is 60 mg.

26. The dosage form of claim 1, wherein the amount of doxycycline of said dosage form is 90 mg.

27. The dosage form of claim 1, wherein the amount of doxycycline of said dosage form is 120 mg.

* * * * *